US007752544B2

(12) United States Patent
Cheng et al.

(10) Patent No.: US 7,752,544 B2
(45) Date of Patent: Jul. 6, 2010

(54) METHOD, SYSTEM, AND APPARATUS FOR REMOTE INTERACTIONS

(75) Inventors: Tsz Cheng, Grand Prairie, TX (US); Hui Lei, Scarsdale, NY (US); Yiming Ye, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 985 days.

(21) Appl. No.: 10/715,041

(22) Filed: Nov. 17, 2003

(65) Prior Publication Data

US 2005/0108660 A1    May 19, 2005

(51) Int. Cl.
*G06F 3/01* (2006.01)
*G06F 19/00* (2006.01)

(52) U.S. Cl. .................. 715/701; 715/716; 715/863; 700/245; 700/264

(58) Field of Classification Search ................ 715/863, 715/701, 702, 704, 716, 753, 760; 700/245, 700/259, 261, 264; 318/568

See application file for complete search history.

(56) References Cited

U.S. PATENT DOCUMENTS

| 3,870,034 | A |   | 3/1975  | James |
|-----------|---|---|---------|-------|
| 5,638,826 | A |   | 6/1997  | Wolpaw et al. |
| 5,676,138 | A |   | 10/1997 | Zawilinski |
| 6,002,808 | A | * | 12/1999 | Freeman ................. 382/288 |
| 6,024,700 | A |   | 2/2000  | Nemirovski et al. |
| 6,028,593 | A | * | 2/2000  | Rosenberg et al. ........ 345/156 |
| 6,053,738 | A |   | 4/2000  | Ivey, Jr. |
| 6,292,713 | B1 | * | 9/2001  | Jouppi et al. ............... 700/245 |
| 6,347,261 | B1 | * | 2/2002  | Sakaue et al. .............. 700/245 |
| 6,428,475 | B1 |   | 8/2002  | Shen |
| 6,714,840 | B2 | * | 3/2004  | Sakaue et al. .............. 700/245 |
| 6,879,862 | B2 | * | 4/2005  | Brown et al. ................. 700/17 |
| 7,027,965 | B2 | * | 4/2006  | Hannaford et al. ............ 703/2 |
| 7,036,094 | B1 | * | 4/2006  | Cohen et al. ................ 715/863 |
| 7,440,819 | B2 | * | 10/2008 | Morel et al. ............... 700/245 |
| 2003/0204384 | A1 | * | 10/2003 | Owechko et al. ............... 703/1 |

OTHER PUBLICATIONS

Hashimoto et al. "Tele-Handshaking through the Internet", IEEE Workshop on Robot and Human Communication, copyright 1996 IEEE, pp. 90-95.*
Rovers et al., "HIM: A Framework for Haptic Instant Messaging", Conference on Human Factors in Computing Systems (CHI '04), extended abstracts on Human factors in computing systems, Apr. 24-29, 2004, Vienna, Austria, pp. 1313-1316.*
DiSalvo et al., "The Hug: An Exploration of Robotic Form for Intimate Conversation", Proceedings of the 2003 IEEE International Workshop on Robot and Human Interactive Communication, Millbrae, California, USA, Oct. 31 - Nov. 2, 2003, pp. 403-408.*
Oakley, I. and O'Modhrain, S. "Contact IM: Exploring asynchronous touch over distance," Proceedings of CSCW, New Orleans, USA, Nov. 16-20, 2002.*

* cited by examiner

*Primary Examiner*—William L Bashore
*Assistant Examiner*—Andrew Tank
(74) *Attorney, Agent, or Firm*—Novak Druce + Quigg LLP (57) ABSTRACT

A method of communicating physical human interactions over a communications network can include detecting physical movement of a user, generating data specifying the physical movement, and determining at least one action indicated by the data. The method further can include transmitting the action over a communications network to a receiving system and simulating the action in the receiving system.

8 Claims, 5 Drawing Sheets

METHOD, SYSTEM, AND APPARATUS FOR REMOTE INTERACTIONS

BACKGROUND

1. Field of the Invention

The invention relates to the field of communications and, more particularly, to communicating physical human interactions from one user to another over a communications network.

2. Description of the Related Art

Most human interactions that take place over a communications network take the form of electronic messages such as electronic mails or instant messages. Other forms of communication provide users with deeper levels of interaction. For example, the use or exchange of audio and/or video data over a communications network can provide an added level of realism and immediacy to communications.

Still other communication systems attempt to enhance user interactions by incorporating sensory stimuli such as smell and taste. One such system can be implemented as a computer system peripheral device that can be activated responsive to control signals received over a communications network. For example, when a user visits a Web site capable of sending appropriately formatted control signals, the peripheral device can activate. The control signals are sent from the Web site or other network location to the user's computer system. The computer system then routes the control signals to the peripheral device. The peripheral device emits the smell and/or taste dictated by the control signals to complement the Web site.

Complementary systems such as this, while adding a level of realism to a user's online experience, do not serve to enhance communications among users. More particularly, such systems are not bi-directional and typically are not activated by a user for the benefit of communicating an action to another user. In consequence, the ability of a user to convey physical actions or gestures over a communications network is limited. That is, the current state of the art does not permit users to send, receive, or exchange physical human interactions such as handshakes, embraces, or the like in any meaningful way.

SUMMARY OF THE INVENTION

The present invention provides a method, system, and apparatus for communicating physical human interactions over a communications network. More particularly, through one or more sensing devices, user motions, gestures, and other physical movements can be detected. The data generated by the sensing devices can be interpreted as a particular action that is encoded as a message. The message is sent to another system via a communications network. Upon receiving the message, the message can be decoded. The receiving system then activates one or more actuators which can simulate the action detected by the sensing devices. The inventive arrangements disclosed herein can be implemented to provide for a uni-directional and/or a bi-directional communication system that is capable of communicating physical human interactions between users.

One aspect of the present invention can include a method of communicating physical human interactions over a communications network. The method can include detecting physical movement of a user, generating data specifying the physical movement, and determining at least one action indicated by the data. The data can be generated by one or more sensors configured to detect physical movement of the user. The action can be transmitted over a communications network to a receiving system which can simulate the action. The action can be simulated by performing the action on a second user located at the receiving system.

The method also can include, after the determining step, converting the data to markup language formatted data. Accordingly, the markup language formatted data can be processed in the receiving system to identify the action. The markup language formatted data can specify at least one actuator movement to be implemented by the receiving system and an amount of force to be applied by the actuator or actuators. Thus, the simulating step can include activating at least one actuator to simulate the action on the second user. The simulation step further can include translating the action into instructions for activating at least one actuator and activating the actuator or actuators in accordance with the instructions.

The method further can include detecting physical movement of a user in the receiving system, generating data specifying the physical movement in the receiving system, and determining at least one action indicated by the data. The action can be transmitted over a communications network to a sending system, which can then simulate the action.

Another aspect of the present invention can include a system for communicating physical human interactions over a communications network. The system can include at least one sending sensor configured to detect physical movement of a first user and a sending message transmission module. The sending message transmission module can be configured to receive data from one or more of the sending sensors and determine an intended action. The sending message transmission module further can transmit the action to another system over a communications network.

The system also can include a receiving message transmission module. The receiving message transmission module can be configured to receive the action over the communications network and translate the action into instructions for activating at least one actuator. Thus, the system further can include one or more receiving actuators configured to simulate the action on a second user.

In another embodiment of the present invention, the system can include at least one sending actuator coupled with the sending message transmission module. The sending actuators can be configured to simulate, on the first user, actions originating in the receiving message transmission module. The system also can include at least one receiving sensor configured to detect physical movement of the second user. The receiving sensors can be communicatively linked with the receiving message transmission module.

BRIEF DESCRIPTION OF THE DRAWINGS

There are shown in the drawings, embodiments which are presently preferred, it being understood, however, that the invention is not limited to the precise arrangements and instrumentalities shown.

DETAILED DESCRIPTION OF THE INVENTION

Figure 1:
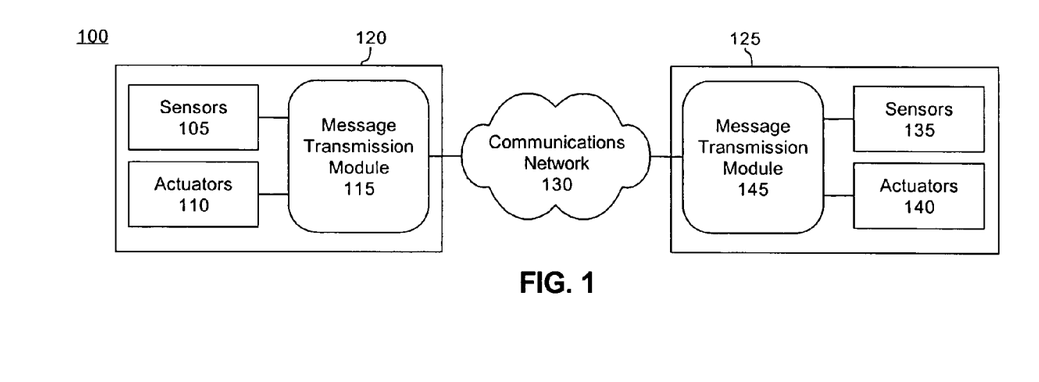
FIG. 1 is a schematic diagram illustrating a system for communicating physical human interactions from one user to another over a communications network in accordance with one embodiment of the present invention.

FIG. 1 is a schematic diagram illustrating a system 100 for communicating physical human interactions from one user to another over a communications network in accordance with one embodiment of the present invention. As shown, system 100 can include a first interaction system 120 that is communicatively linked with a second interaction system 125 via a communications network 130.

The first interaction system 120 can include one or more sensors 105, one or more actuators 110, and a message transmission module (MTM) 115. Similar to the first interaction system 120, the second interaction system 125 can include one or more sensors 135, one or more actuators 140, and a MTM 145. The communications network 130 can be implemented as a local area network (LAN), a wide area network (WAN), the World Wide Web, the Internet, an intranet, the public switched telephone network, one or more wireless networks, combinations thereof, or any other suitable network over which information can be exchanged.

The sensors 105 and 135 can be any of a variety of sensors capable of detecting physical movement of a user. For example, the sensors can be motion sensors or sound sensors such as transducive elements or microphones. The sensors 105 and 135 also can be optical sensors capable of detecting changes in a user's facial expression or the motion of a part of the user's body or entire body. Other examples of sensors can include pressure or force sensors capable of detecting the amount of force applied to the sensor by a user.

According to one embodiment of the present invention, the sensors 105 and 135 can be incorporated into models of human hands or other body parts such as human heads and/or faces. A model, for example a model of a human hand, can include multiple sensors located throughout. The sensors can be placed such that when a user touches the hand model, for instance in the context of a handshake, the sensors can detect contact with the user's hand as well as the amount of force applied to the various portions of the model within which the sensors 105 and 135 are disposed. The sensors 105 and 135 can generate time varying data specifying the amount of force applied to each sensor over time as well as the particular locations of the model that force was applied. That is, each sensor 105 and 135 can send an identifier along with detected data that uniquely identifies that sensor. The sensor identifier can be associated with a known position within the model, such as the index finger, palm, back of the hand, or the like. Accordingly, the sensor data can be correlated with the activation of a particular sensor or set of sensors disposed within a particular portion or location of the model.

It should be appreciated that the sensors 105 can be included within any of a variety of different models, and that the particular type of model used, or framework for housing the sensors, is not a limitation of the present invention. For example, in one embodiment, the model can be a particular portion of the human body or the entire human body. Additionally, other sensors such as motion sensors and/or audio sensors can be disposed within the model, on the outside of the model, and/or in the same environment as the model, for example to sense ambient noise in a room. In any case, data generated by the sensors 105 and 135 can be transmitted to each MTM 115 and 145 respectively. The sensors 105 and 135 can each transmit data to MTM 115 and 145 respectively via wired or wireless communications links. If necessary, a signal mixer or routing system (not shown) can be incorporated between the sensors and the MTM's.

The actuators 110 and 140 can be configured to respond to control signals received from MTM's 115 and 145 respectively. The actuators 110 and 140 can apply force or cause a model to apply force, for example to a user, responsive to the received control signals. While each actuator can be implemented as a separate mechanism designed to perform a particular function, such as apply force to a user's back to simulate a slap or pat on the back, one or more actuators also can be included within a model of a human body or within a model of a portion of a human body.

For example, the actuators 110 and 140 can be disposed within a model of a human hand, a human head, or an entire human body. As such, each actuator or set of actuators can cause movement of the portion of the model within which the actuator is disposed. Accordingly, upon activation, the models can simulate physical actions of a human being such as the movement of a hand, a head, a particular facial expression, an embrace, or the like. Like the sensors 105 and 135, the actuators 110 and 140 can be communicatively linked with the MTM 115 and 145 respectively via wired and/or wireless communications links. A signal mixer or routing system (not shown), whether the same unit or a different unit as may be used with regard to the sensors, also can be incorporated between the actuators and the MTM if necessary.

Each of the MTM's 115 and 145 can be implemented as an application or program executing within a suitable information processing system, such as a computer, a portable computer, a personal digital assistant, or the like. The MTM's 115 and 145 can receive data from sensors 105 and 135 respectively. From the received data, each MTM 115 and 135 can determine the action that was intended by a user. The MTM's 115 and 135 can then encode the data to specify the user intended action. The action is forwarded as a message to another MTM for interpretation. Thus, a receiving MTM can determine which actuators to activate to simulate the received action.

In operation, a user can perform an action such as a handshake on a model of a human or a human hand. The sensors 105 disposed within the model can detect the portions or locations on the model to which the user applied force, the amount of force applied over time, and therefore, the duration force was detected by each sensor 105. Each sensor 105 can be configured to generate and send data when a force is detected. The generated data can specify a time the force was detected, the amount of force detected, and the body part (or sensor identifier) to which force was applied.

In illustration, if the model is a human hand, sensors 105 can be disposed in each finger, in the palm of the hand, on the back of the hand, or in any other portions of the model hand as may be required depending upon the level of granularity of the model and data to be produced. For example, a model can be built such that each finger has multiple sensors, the palm of the hand has multiple sensors, etc. When force is detected and a sensor is activated, the sensor can periodically send data, for example each second, or fraction thereof.

The data generated by each of the sensors 105 can be sent to the MTM 115. The MTM 115 then analyzes the received data to determine the action that was intended by the user. In particular, the MTM 115 can determine that, based on the sensors 105 that were activated, the force applied, and duration of the detected force, the intended action was a long-hard handshake, a soft-short handshake, or some other action such as a hug or pat on the back.

The MTM 115 can encode the received data into one or more messages having an intermediate data format for transmission over the communications network 130 to the MTM 145. The intermediate data format can specify the particular action that was interpreted by the MTM 115. According to one embodiment of the present invention, the intermediate data format can be a markup language suited for communicating human to human interactions, and particularly, physical interactions.

The MTM 145 can receive the message or messages from the MTM 115 and determine the action specified. The MTM 145 then can determine which actuators 140 should be activated to replicate or simulate the action received from the MTM 115. The MTM 145 can be programmed with rules specifying how to implement each particular action. Based upon the received action, the rules can dictate which actuators to activate, the time each actuator should be activated, the amount of force to be used by each actuator, and how the force varies over time. Accordingly, the MTM 115 can send appropriate control signals to each actuator 140 that is necessary to simulate the received action.

Taking the previous example, the MTM 145 can determine that the received action is a handshake. The MTM 145 then can determine the actuators necessary to simulate the long-hard, or soft-short handshake. The MTM 145 then sends control signals to each necessary actuator to simulate the action taken by the user interacting with the sensors 105.

While not shown, it should be appreciated that the system 100 can support two-way, or bidirectional communications. That is, a user that interacts with actuators 140 in the second interaction system 125 can respond with another physical gesture that will be detected by sensors 135 and relayed to the MTM 145, the MTM 115, and finally enacted by the actuators 110.

The system 100 can be implemented in any of a variety of different configurations. In one embodiment, each MTM 115 and 145 can be disposed within an information processing system and the respective sensors 105 and 135 can be implemented as separate mechanisms. In another embodiment, the sensors and the actuators can be combined into a more complex system, such as a robotic member or model that communicates with the MTM. In yet another embodiment, the MTM, the sensors, and the actuators can be included within a single mechanism such as a robot with information processing capability. Still, as noted, the system 100 can be implemented such that one or more of the elements described herein are combined into a single unit, while other elements, such as particular sensors and/or actuators, are disposed within a separate unit, with each being communicatively linked to the appropriate MTM.

Figure 2:
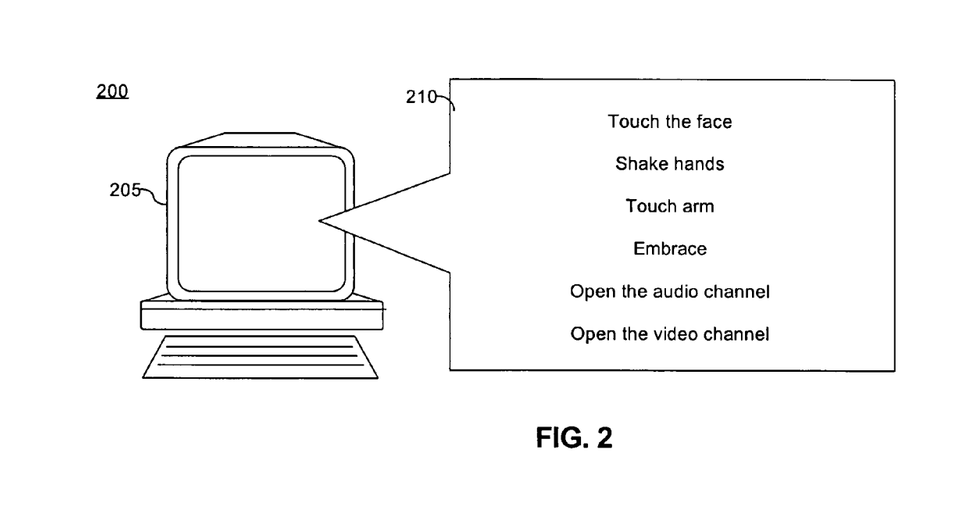
FIG. 2 is a schematic diagram illustrating one embodiment of the message transmission module described in FIG. 1.

FIG. 2 is a schematic diagram illustrating one embodiment of the MTM described in FIG. 1. The MTM can be implemented as software executing within an information processing system 205 as shown. In addition to the functions previously described, the MTM also can provide a visual interface through which a user can interact or initiate particular actions and physical interactions. The MTM can provide a graphical user interface (GUI) 210 within which the user can select one or more physical human actions and/or processing tasks. The GUI 210 can be presented upon a display, so that the user can make selections using a pointing device or keyboard. A touch screen also can be used such that the user can point to the desired selection.

For example, as shown, selections such as "touch the face", "shake hands", "touch arm", or "embrace" can be selected. Selection of a particular action can circumvent the action detection process so that the MTM automatically generates an encoded message, for instance using a suitable markup language, and sends the message to another MTM for execution. In that case, no interpretation of sensor data is necessary as the user directly specified a desired or intended action. Other processing tasks such as opening an audio channel and/or a video channel between the MTM and another MTM over a communications network can be selected and initiated as well.

Figure 3:
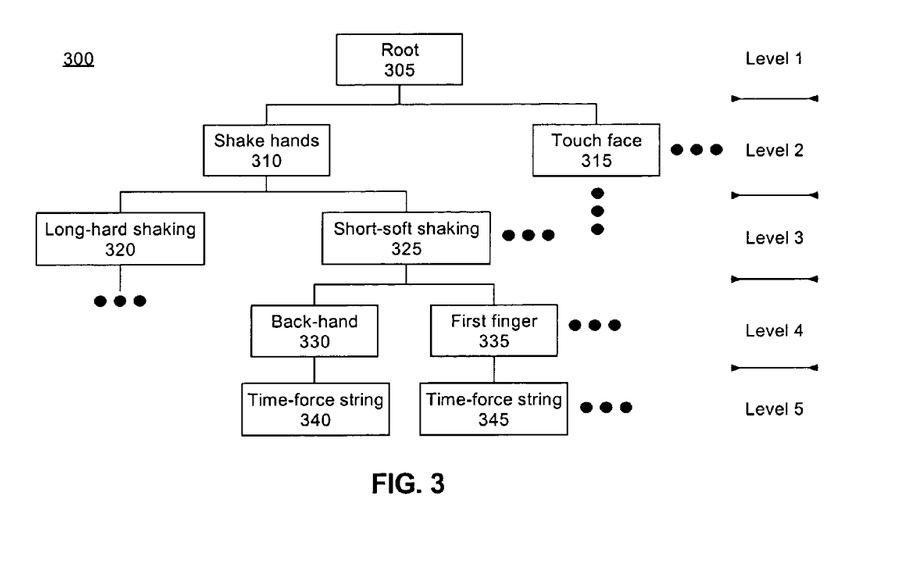
FIG. 3 is a schematic diagram illustrating a hierarchical data structure that can be used with the system of FIG. 1 to describe physical human interactions.

FIG. 3 is a schematic diagram illustrating one embodiment of a hierarchical data structure (data hierarchy) 300 that can be used with the system of FIG. 1 to describe physical human interactions. The data hierarchy 300 can be used by an interaction system that is interpreting sensor data to encode an action to be sent to another interaction system. The sending interaction system, and specifically the MTM, can formulate appropriate markup language messages specifying one or more actions perceived by the MTM using the data hierarchy 300, also referred to as the sending data hierarchy. The markup language used can be any of a variety of different markup languages including, but not limited to, proprietary or custom implementations of extensible markup language (XML).

Still, other known markup languages can be used and/or incorporated if necessary or desired. For example, Virtual Human Markup Language (VHML) can be used or incorporated, as well as any of the constituent parts of VHML such as Dialogue Manager Markup Language (DMML), Facial Animation Markup Language (FAML), Body Animation Markup Language (BAML), Speech Markup Language (SML), Emotion Markup Language (EML), and HyperText Markup Language (HTML).

As shown, the data hierarchy 300 begins with a root node 305 on the level 1. Level 2 specifies the possible range of human actions and/or interactions that can be conveyed through the system of FIG. 1. Examples of general interactions can include, but are not limited to, shake hands 310 and touch face 315. Level 3 further classifies the general categories of interactions into more specific instances of each. For example, as shown, shake hands 310 can be subdivided into 2 different subcategories: long-hard shaking 320 and short-soft shaking 325.

In level 4, each subcategory further can be divided into segments or portions of a model, in this case a model of a human hand, that must be activated to accomplish the action specified in level 3. Each portion of the model identified in level 4 can be associated with a sensor, or a set of sensors, for detecting human actions performed on that particular segment of the model. Thus, implementing a short-soft shaking 325 can involve at least activating the child nodes corresponding to the back-hand 330 portion of the model, the first finger 335 portion of the model, as well as any other portions of the hand model that may be necessary. Beneath each portion of the hand model, occupying level 5, are nodes 340 and 345 which specify time-force strings. More particularly, each of nodes 340 and 345 can specify one or more time values and associated force values, or ranges of time and force values, that indicate how long a particular level of force should be applied by an actuator responsible for activating the portion of the hand model indicated by the parent node of the time-force string node.

Figure 4:
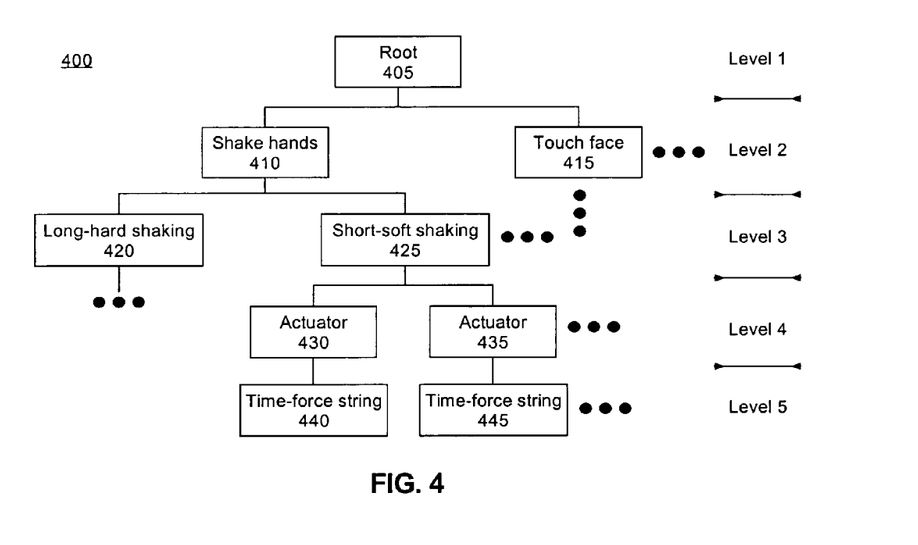
FIG. 4 is a schematic diagram illustrating a hierarchical data structure that can be used with the system of FIG. 1 to decode received actions into specific actuator movements.

FIG. 4 is a schematic diagram illustrating one embodiment of a hierarchical data structure (data hierarchy) 400 that can be used with the system of FIG. 1 to convert received actions into specific actuator movements. The data hierarchy 400 can be used by a MTM within an interaction system that is receiving encoded actions. The hierarchy 400 can be used to decode the received encoded actions. Levels 1-3 of the data hierarchy 400 are similar to those of FIG. 3 in that the data hierarchy 400 has a root 405 in level 1, general actions of shake hands 410 and touch face 415 in level 2, and specific types of each general action in level 3. For example, level 3 includes a long-hard shaking node 420 and a short-soft shaking node 425.

In level 4, however, beneath each specific type of action node, the particular actuators to be activated to perform the specified action can be listed. Thus, to implement short-soft shaking 425, actuators 430 and 435 must be activated. Each actuator 430 and 435 is activated according to time force string nodes 440 and 445 respectively.

It should be appreciated by those skilled in the art that the hierarchies depicted in FIGS. 3 and 4 are shown for purposes of illustration only. Each can include more actions or fewer actions as the case may be. Further, each can include greater detail in accordance with the complexity and number of sensors used.

Below is an exemplary listing of Hypertext Human Remote Interaction Modeling Language (HHRIML) which illustrates some aspects of the hierarchies shown in FIGS. 3 and 4.

```
<HHRIML Version 1>
   <Action-Categorization>
   <shake-hands>
      <long-hard-shaking>
      </ long-hard-shaking>
      <short-soft-shaking>
         <back-hand>
            {[5, <1, 5, back-hand>, <2, 5 back-hand>, <3, 9 back-hand>,
            <4, 9 back-hand>, <5,7, back-hand>]}
         </ back-hand>
         <first finger>
            {[6, <1, 7, back-hand>, <2, 5, back-hand>, <3, 6, back-
            hand>, <4, 5, back-hand>, <5, 7, back-hand>, <6, 6, back-
            hand>]}
         </first finger>
      </short-soft-shaking>
   </shake hands>
   <touch-face>
   </touch-face>
</HHRIML>
```

Figure 5:
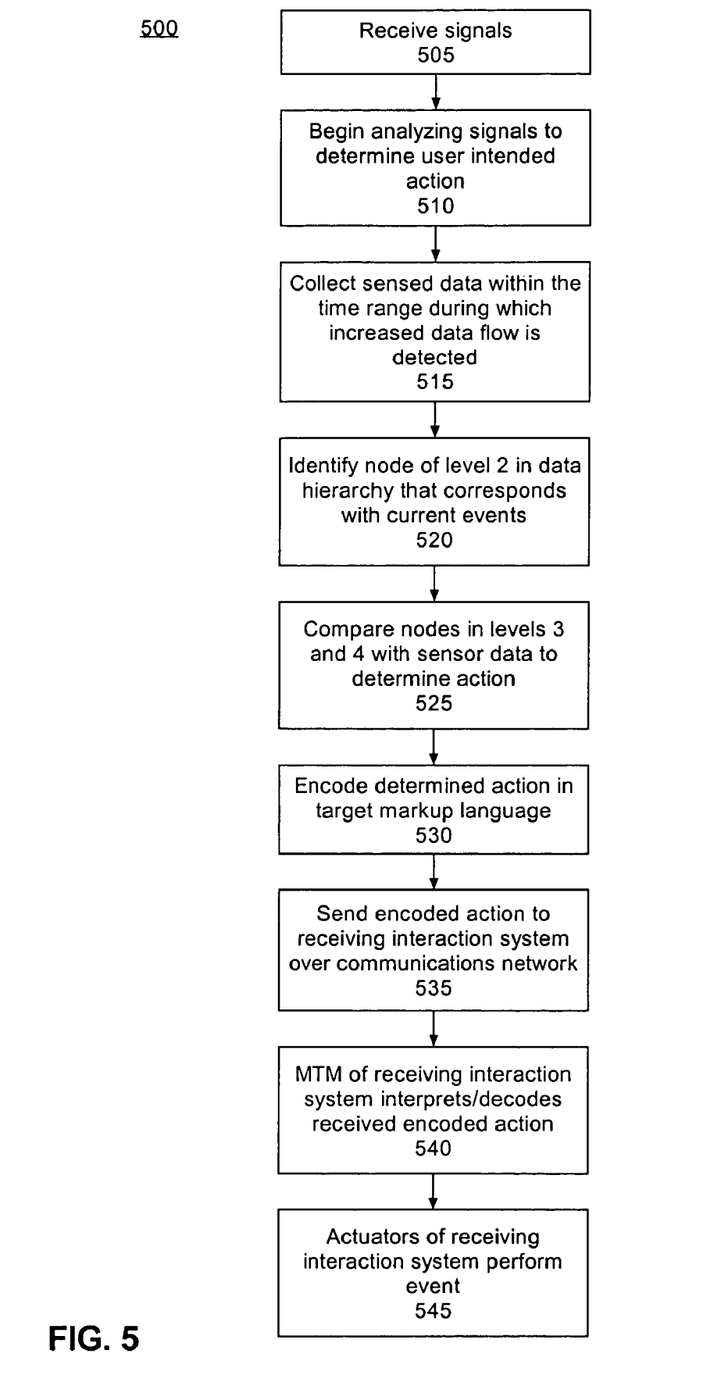
FIG. 5 is a flow chart illustrating a method of communicating physical human interactions from one user to another over a communications network in accordance with one embodiment of the present invention.

FIG. 5 is a flow chart illustrating a method 500 of communicating physical human interactions from one user to another over a communications network in accordance with one embodiment of the present invention. The method 500 can begin in a state where one or more sensors of a sending interaction system have detected physical movement or actions of a user. The sensors can send signals to a MTM of the sending interaction system via a wired or wireless communications link.

While the type of information sent by each sensor can vary with the activity that sensor is designed to detect, in one embodiment of the present invention, the sensors can send information detailing forces detected by each sensor. For example, each sensor can be configured to send information packets formatted as (t, f, l), where t is the time a force is applied, f is the amount of force applied, and l is the location of the force. The time can be measured in any appropriate unit of measure such as seconds or fractions thereof. The location of the force indicates a particular sensor or group of sensors that were activated and sent data.

Accordingly, in step 505, the signals from the sensors can be received in the MTM of the sending interaction system. In step 510, the signals can be analyzed to determine the user intended action and to encode the intended action as a message using a target markup language. The MTM attempts to detect a user's high level intentions, such as shake hands, touch a particular part of the face, etc.

When no user action is performed, the MTM receives a small amount of data over time. When an action is detected, the MTM receives an increased amount of data. The MTM can determine when data corresponding to actions is being received by monitoring the amount of data, for example packets and/or bytes, and determining that when the data rate increases beyond a particular threshold, data corresponding to a user action is being received.

Accordingly, in step 515, the MTM can collect data during a time period within which increased data flow is detected. For example, during a time period starting at $T_1$ and ending at $T_n$, data can be collected in the form of $\Omega=(t_1, f_1, l_1), (t_2, f_2, l_2), \ldots (t_n, f_n, l_n)$. It should be appreciated that more than one sensor can be activated at one time. Accordingly, the MTM can receive data from multiple sensors concurrently. As noted, each l in the data set $\Omega$ corresponds to a particular part of the body. Each node within level 2 of the sending data hierarchy illustrated in FIG. 3 also corresponds to a particular part of the body. Thus, in step 520, the MTM can determine which nodes of level 2 correspond to the received sensor data.

In step 525, the nodes existing with each branch of the sending data hierarchy extending from the nodes identified in step 520 can be compared with the sensor data. The nodes of level 3 and 4 can be used to resolve any ambiguity as to which node of level 2 most closely corresponds with the received sensor data. By matching the data to the nodes of level 3 and 4, the specific action intended by the user can be identified.

In step 530, the determined action can be encoded using a target markup language. The time-force strings indicated by the received sensor data are encoded for each actuator or actuator set. In step 535, the encoded action can be transmitted over a communications network to a receiving interaction system. In step 540, the MTM of the receiving interaction system can receive and decode the encoded message. More particularly, the receiving MTM can parse any received messages specifying actions that are formatted in the target markup language. Thus, the receiving MTM can identify the particular portions of a model, and corresponding actuators, that must be activated to simulate the decoded action as well as the force to be applied by each actuator or set of actuators over a given period of time. Accordingly, in step 545, the actuators of the receiving interaction system that were identified in step 540 can be activated to perform or simulate the decoded action.

Figure 6:
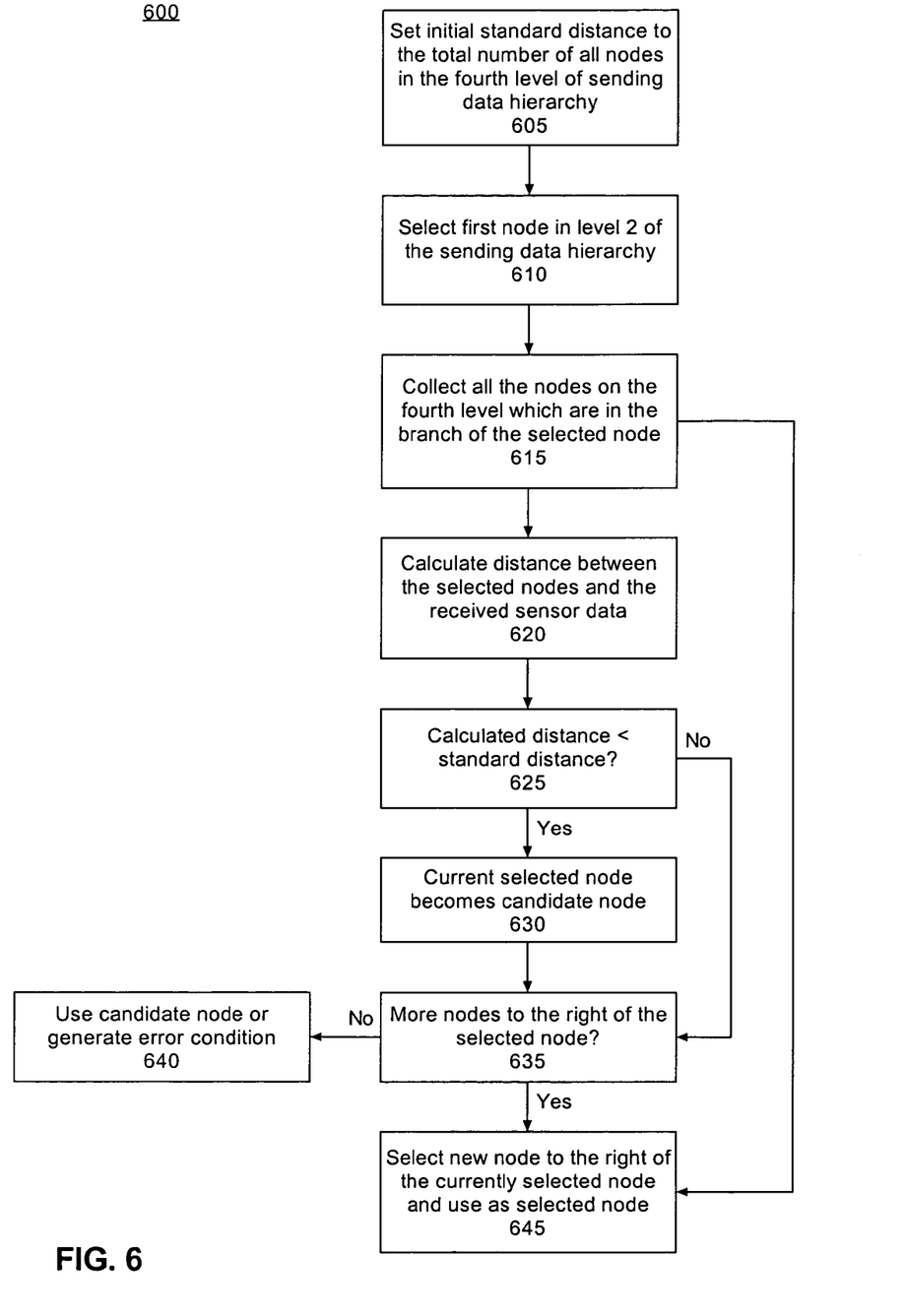
FIG. 6 is a flow chart illustrating one embodiment of a method for determining a user intended action using a hierarchical data structure in accordance with the inventive arrangements disclosed herein.

FIG. 6 is a flow chart illustrating one embodiment of a method 600 for determining a user intended action using a data hierarchy in accordance with the inventive arrangements disclosed herein. More particularly, the method 600 can be used in determining which node of the second level of the sending data hierarchy of FIG. 3 corresponds to the received sensor data. The method 600 uses a distance measure to identify a user intended action from the data hierarchy.

Recalling that the received sensor data can be in the form of (t, f, l), where t is the time a force is applied, f is the amount of force applied, and l is the location or body part detecting the force, the received sensor data defines the set of body parts involved in the detected action. Notably, the set of body parts involved in the action can be less than the body parts specified by the fourth level of the receiving data hierarchy. That is the number of body parts N* involved in a detected user action such as a handshake can be less than or equal to the total number of body parts N that can be used or sensed by the system for a handshake. The body parts indicated by the received sensor data can be represented as the set $L^* = (l^*_1, \ldots, l^*_n)$.

In step 605, an initial standard distance can be set to the total number of all nodes in the fourth level of the sending interaction system data hierarchy (N). In step 610, the first node, for example the leftmost node, in the second level of the sending data hierarchy can be selected. In step 615, all of the nodes that are in the fourth level of the sending data hierarchy that are also within the branch that starts with the selected node are identified or collected. These nodes specify all of the parts that participate in the kind of human to human interaction specified by the selected node and can be referred to as the set $L = (l_1, \ldots, l_n)$.

In step 620, the distance between the selected nodes and the received sensor data can be calculated. The distance can be calculated as the total number of elements that are in L and not in L*, plus the total number of elements that are in L* and not L. In step 625, the calculated distance is compared with the standard distance. If the calculated distance is less than the standard distance, the method can proceed to step 630, where the selected node in the second level of the sending data hierarchy becomes the candidate node. If the calculated distance is not less than the standard distance, the method can proceed to step 635.

In step 635, whether the method has progressed from step 625 or step 630, a determination can be made as to whether any additional nodes to the right of the selected node in the second level of the sending data hierarchy exist. If so, the method can proceed to step 645 to select the next node to the right and continue processing to determine whether that node or any other nodes are candidates. If no further nodes are left to be processed, the method can proceed to step 640. Thus, in step 640, if a candidate node exists, that node can be identified as the intended user action. If no candidate node exists, then an error condition can be generated.

Figure 7:
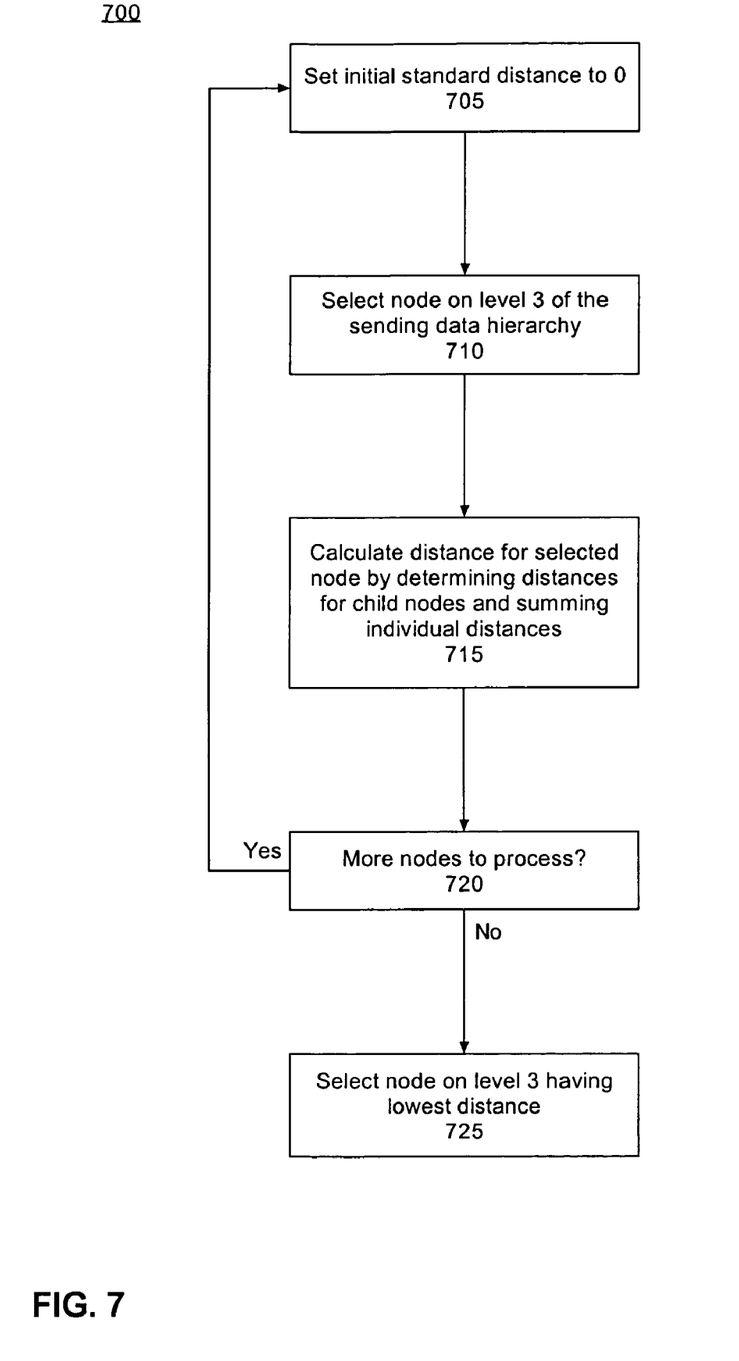
FIG. 7 is a flow chart illustrating another embodiment of a method for determining a user intended action using a hierarchical data structure in accordance with the inventive arrangements disclosed herein.

FIG. 7 is a flow chart illustrating another embodiment of a method 700 for determining a user intended action using a hierarchical data structure in accordance with the inventive arrangements disclosed herein. The method 700 can be used in determining which node of the third level of the sending data hierarchy of FIG. 3 corresponds to the received data. The method can begin in a state where sensor data has been received. In step 705, the initial standard distance can be set to 0. In step 710, a first node on the third level of the sending data hierarchy can be selected. According to one embodiment of the present invention, the leftmost node can be selected.

In step 715, the distance for the selected node can be calculated. The distance can be calculated by determining a distance measure for each child node (in level 4) of the selected node in level 3 and then summing the individual distances of the child nodes for the selected node. The set of forces received from the sensor data, denoted as $F = (f^*_1, \ldots, f^*_n)$, can be compared with the child nodes of the selected node. A distance value can be determined for each member of F. Each member of the set F can be compared with predetermined, allowable or average time-force strings of the sending data hierarchy. That is, the sending data hierarchy can specify allowable time-force strings as a series of one or more values, a range of possible values, or the like. In the event no match is found between a member of the set of forces F and the time-force strings of the sending data hierarchy, the distance can be set to the value of the member of F that was compared. For example, if force $f^*_1$ was compared with the time-force strings and no match was found, the distance for that member of set F can be $f^*_1$.

If a match is determined for a member of the set, the distance can be calculated as follows: $[ABS(f^*_{match} - f_{match})/(f^*_{match} + f_{match})]*f_{match}$, where $f^*_{match}$ is the force component of the sensor data that was found to match the force component in the sending data hierarchy and $f_{match}$ is the matching force component from the sending data hierarchy. Each individual distance calculated for the members of the set F can be summed. The total distance is the distance for the selected node, that is the node selected in step 710.

In step 720, a determination can be made as to whether any additional nodes in the third level of the sending data hierarchy have yet to be processed. If so, the method can store the distance and continue to step 705 to continue calculating distances for remaining nodes of level 3 in the sending data hierarchy. If not, the node in level 3 having the lowest distance can be selected as the user intended action.

According to one embodiment of the present invention, the methods described in reference to FIGS. 6 and 7 can be used individually to determine a user intended action. While FIG. 6 illustrates a method of determining a more general user action, FIG. 7 provides a method of determining a more specific user action. Accordingly, in another embodiment of the present invention, the two methods can be used in combination with one another to determine a user intended action and/or to verify results. In any case, it should be appreciated that the present invention is not limited to one particular technique for determining user intended actions. Rather, any of a variety of suitable processing techniques can be applied.

The present invention provides a method, system, and apparatus for exchanging physical human interactions between users over a communications network. In accordance with the present invention, user movements or actions detected by sensors can be encoded and transmitted over a communications network to a processing system. The processing system can decode the encoded actions and activate one or more actuators to simulate the user movements detected by the sensors. The actuators can simulate the movements of the user upon a different user.

The present invention can be realized in hardware, software, or a combination of hardware and software. The present invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The present invention also can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

This invention can be embodied in other forms without departing from the spirit or essential attributes thereof. Accordingly, reference should be made to the following claims, rather than to the foregoing specification, as indicating the scope of the invention.

What is claimed is:

1. A method of bi-directionally communicating physical human interactions between users over a communications network comprising:
- performing a first action on a first model by a first user located at a first interaction system, said first interaction system including one or more sensors, one or more actuators, and a first message transmission module, said first model representing at least a portion of a human body including at least one among a human head, a human face, a human back and an entire human body, wherein said first model incorporates one or more sensors disposed at various portions or locations within or on the first model, wherein the first action of the first user includes at least one body movement of the first user and a change in facial expression of the first user, and wherein the at least one body movement and the change in facial expression are selectable by the first user through a visual interface;
- detecting portions or locations within or on the first model to which the first user applied force and an amount of force applied over time by each sensor, each sensor being configured to generate and send data to the first message transmission module when a force is detected, the generated data specifying a duration of the force detected, the amount of the force detected, and the portion or location within or on the first model to which the force was applied;
- the first message transmission module collecting and analyzing the data generated by each sensor and determining the first action intended by said first user;
- the first message transmission module converting the data to markup language formatted data and encoding the data into one or more messages for transmitting the determined action over the communications network to a second interaction system, said second interaction system being communicatively linked with the first interaction system via the communications network, said second interaction system including one or more sensors, one or more actuators, and a second message transmission module;
- the second message transmission module receiving and interpreting the one or more messages by processing the markup language formatted data encoded in the one or more messages to determine the first action specified by the one or more messages;
- simulating the first action by performing said first action on a second user at the second interaction system using a second model by activating one or more actuators incorporated in the second model, said second model representing at least said portion of said human body;
- performing a second action on the second model by the second user in response to the first action, wherein said second model incorporates one or more sensors disposed at various portions or locations within or on the second model;
- generating data from activated sensors within or on the second model specifying the second action and send the data to the second message transmission module;
- the second message transmission module collecting and analyzing the data generated by each of the activated sensor within or on the second model and determining the second action intended by said second user;
- the second message transmission module converting the data to markup language formatted data and encoding the data into one or more messages for transmitting the determined second action over the communications network to the first interaction system; and
- simulating the second action by performing said second action on the first user at the first interaction system using the first model, wherein said first model incorporates the one or more actuators.

2. The method of claim 1, wherein the markup language formatted data specifies at least one actuator movement to be implemented by the second model and an amount of force to be applied in the at least one actuator movement.

3. The method of claim 1, said simulating step further comprising the step of translating the action into instructions for activating at least one actuator; and activating the at least one actuator in accordance with the instructions.

4. The method of claim 1, wherein said generated data specifies a time when a force was detected, the amount of said force, and a location on said human body to which said force was applied.

5. The method of claim 1, wherein said action intended by said first user includes at least one among an embrace, a slap on the back, and a pat on the back.

6. The method of claim 1, further comprising:
- providing a graphical user interface, within said graphical user interface said first user can select human actions or processing tasks, wherein said human actions include at least one among "touch the face", "touch arm", and "embrace" and said processing tasks include at least one of "opening an audio channel" and "opening a video channel".

7. A system for bi-directionally communicating physical human interactions between users over a communications network comprising:
- a first interaction system and a second interaction system communicatively linked via the communications network;
- wherein the first interaction system includes:
  - a first model upon which a first action is performed by a first user, the first model representing a portion of a human body representing at least one among a human head, a human face, a human back and an entire human body;
  - at least one sensor disposed at various portions or locations within or on the first model and configured to detect physical movement of the first user, wherein the physical movement of the first user includes at least one body movement of the first user and a change in facial expression of the first user, wherein portions or locations within or on the first model to which the first user applied force and an amount of force applied over time are detected by each sensor, each sensor being configured to generate and send data when a force is detected, the generated data specifying a during of the force detected, the amount of force detected, and the portion or location to which force was applied;
  - a first message transmission module for collecting and analyzing the data generated by each sensor and determining the first action intended by the first user, and for converting the data to markup language formatted data and encoding the data into one or more messages for transmitting the determined first action over the communications network to the second interaction system, wherein the first message transmission module has a visual interface through which the first user can select the at least one body movement and the change in facial expression; and at least one actuator incorporated within or on the first model to simulate any action received at the first interaction system via the communications network;

the second interaction system includes:

a second message transmission module for receiving and interpreting the one or more messages to determine the first action specified by the one or more messages;

a second model incorporating at least one actuator configured to simulate the first action to a second user at the second interaction system, the second model representing at least the portion of the human body; and at least one sensor disposed at various portions or locations within or on the second model, wherein the at least one sensor detects a second action of the second user in response to the first action.

8. A computer readable storage medium, having stored thereon a computer program having a plurality of code sections executable by a machine for causing the machine to perform the steps of:

performing a first action on a first model by a first user located at a first interaction system, said first interaction system including one or more sensors, one or more actuators, and a first message transmission module, said first model representing at least a portion of a human body including at least one among a human head, a human face, a human back and an entire human body, wherein said first model incorporates one or more sensors disposed at various portions or locations within or on the first model, and wherein the first action of the first user includes at least one body movement of the first user and a change in facial expression of the first user, and wherein the at least one body movement and the change in facial expression are selectable by the first user through a visual interface;

detecting portions or locations within or on the first model to which the first user applied force and an amount of force applied over time by each sensor, each sensor being configured to generate and send data to the first message transmission module when a force is detected, the generated data specifying a duration of the force detected, the amount of the force detected, and the portion or location within or on the first model to which the force was applied;

the first message transmission module collecting and analyzing the data generated by each sensor and determining the first action intended by said first user;

the first message transmission module converting the data to markup language formatted data and encoding the data into one or more messages for transmitting the determined action over a communications network to a second interaction system, said second interaction system being communicatively linked with the first interaction system via the communications network, said second interaction system including one or more sensors, one or more actuators, and a second message transmission module;

the second message transmission module receiving and interpreting the one or more messages by processing the markup language formatted data encoded in the one or more messages to determine the first action specified by the one or more messages;

simulating the first action by performing said first action on a second user at the second interaction system using a second model by activating one or more actuators incorporated in the second model, said second model representing at least said portion of said human body;

performing a second action on the second model by the second user in response to the first action, wherein said second model incorporates one or more sensors disposed at various portions or locations within or on the second model;

generating data from activated sensors within or on the second model specifying the second action and send the data to the second message transmission module;

the second message transmission module collecting and analyzing the data generated by each of the activated sensor within or on the second model and determining the second action intended by said second user;

the second message transmission module converting the data to markup language formatted data and encoding the data into one or more messages for transmitting the determined second action over the communications network to the first interaction system; and simulating the second action by performing said second action on the first user at the first interaction system using the first model, wherein said first model incorporates the one or more actuators.

* * * * *